United States Patent
Gordon et al.

(10) Patent No.: US 9,786,481 B2
(45) Date of Patent: Oct. 10, 2017

(54) AUTOMATED CLEANLINESS DIAGNOSTIC FOR MASS SPECTROMETER

(71) Applicant: Micromass UK Limited, Wilmslow (GB)

(72) Inventors: David Gordon, Manchester (GB); Daniel James Kenny, Knutsford (GB); Richard Barrington Moulds, Stockport (GB)

(73) Assignee: Micromass UK Limited, Wilmslow (GB)

( * ) Notice: Subject to any disclaimer, the term of this patent is extended or adjusted under 35 U.S.C. 154(b) by 0 days.

(21) Appl. No.: 15/023,022

(22) PCT Filed: Sep. 17, 2014

(86) PCT No.: PCT/GB2014/052817
§ 371 (c)(1),
(2) Date: Mar. 18, 2016

(87) PCT Pub. No.: WO2015/040385
PCT Pub. Date: Mar. 26, 2015

(65) Prior Publication Data
US 2016/0233073 A1    Aug. 11, 2016

(30) Foreign Application Priority Data

Sep. 20, 2013 (EP) ..................... 13185291
Sep. 20, 2013 (GB) ................... 1316688.9

(51) Int. Cl.
*H01J 49/24* (2006.01)
*F04C 28/02* (2006.01)
(Continued)

(52) U.S. Cl.
CPC .............. *H01J 49/24* (2013.01); *F04C 28/00* (2013.01); *F04C 28/02* (2013.01); *G01L 19/08* (2013.01);
(Continued)

(58) Field of Classification Search
None
See application file for complete search history.

(56) References Cited

U.S. PATENT DOCUMENTS 5,043,576 A     8/1991  Broadhurst et al.
6,809,316 B2 *  10/2004 Kato ................... H01J 49/0031
                                                         250/281
(Continued)

FOREIGN PATENT DOCUMENTS

JP          62130149        6/1987
JP          0462749         2/1992
(Continued)

*Primary Examiner* — Jack Berman
(74) *Attorney, Agent, or Firm* — Diederiks & Whitelaw, PLC

(57) ABSTRACT

A mass spectrometer or ion mobility spectrometer is disclosed comprising means for detecting a blockage in an inlet orifice arranged between an ion source and a vacuum chamber. The blockage is detected as a result of a reduction in pressure within the vacuum chamber. This change in pressure is detected indirectly by monitoring the amount of power that a vacuum pump is using, the amount of current that a vacuum pump is drawing, the temperature of a vacuum pump or a region in proximity to the vacuum pump, or the flow rate of gas out of a vacuum pump.

16 Claims, 1 Drawing Sheet

(51) Int. Cl.
  *F04C 28/00*   (2006.01)
  *G01L 19/08*   (2006.01)
  *G01N 27/62*   (2006.01)
  *H01J 49/00*   (2006.01)
  *H01J 49/06*   (2006.01)

(52) U.S. Cl.
  CPC ........ *G01N 27/622* (2013.01); *H01J 49/0013* (2013.01); *F04B 2205/112* (2013.01); *H01J 49/067* (2013.01)

(56) References Cited

U.S. PATENT DOCUMENTS

| | | | | |
|---|---|---|---|---|
| 7,886,692 | B2* | 2/2011 | Stellnert | A01J 5/007 |
| | | | | 119/14.08 |
| 8,987,664 | B2* | 3/2015 | Sugawara | H01J 49/005 |
| | | | | 250/281 |
| 9,008,847 | B2 | 4/2015 | Clausmann et al. | |
| 2006/0289743 | A1* | 12/2006 | Hasegawa | H01J 49/4265 |
| | | | | 250/288 |
| 2008/0063534 | A1* | 3/2008 | Nakayama | F04C 28/02 |
| | | | | 417/6 |

FOREIGN PATENT DOCUMENTS

| | | |
|---|---|---|
| JP | 06203790 | 7/1994 |
| JP | 2002/350008 | 12/2002 |
| JP | 2008/095504 | 4/2008 |
| JP | 2012/043672 | 3/2012 |

\* cited by examiner

AUTOMATED CLEANLINESS DIAGNOSTIC FOR MASS SPECTROMETER

CROSS REFERENCE TO RELATED APPLICATION APPLICATIONS

This application is the National Stage of International Application No. PCT/GB2014/052817, filed 17 Sep. 2014 which claims priority from and the benefit of United Kingdom patent application No. 1316688.9 filed on 20 Sep. 2013 and European patent application No. 13185291.5 filed on 20 Sep. 2013. The entire contents of these applications are incorporated herein by reference.

BACKGROUND OF THE INVENTION

The present invention relates to mass spectrometer or ion mobility spectrometer that is able to automatically determine and indicate when it is required to be cleaned.

It can be time consuming and difficult to diagnose and isolate the cause of poor sensitivity or lack of signal in a mass spectrometer or ion mobility spectrometer. Such problems can lead to an engineer having to visit the customer site and may also lead to users wasting sample sets before they realise that there is a problem with the instrument. Problems such as these increase the downtime of the instruments and ultimately increase the cost of their ownership. An automated technique of diagnosing such issues and providing the user with information on how to rectify them would therefore be highly advantageous.

It is therefore desired to provide an improved mass spectrometer or ion mobility spectrometer and an improved method of operating such a spectrometer.

SUMMARY OF THE INVENTION

From a first aspect the present invention provides a mass spectrometer or ion mobility spectrometer comprising:
an ion source;
a first vacuum chamber;
a first vacuum pump for maintaining the pressure within the vacuum chamber lower than the pressure outside of the chamber;
an inlet orifice arranged between the ion source and the vacuum chamber for allowing ions to pass from the ion source into the vacuum chamber;
a second vacuum pump and a second vacuum chamber, wherein the second vacuum pump is arranged and configured for pumping gas from the second vacuum chamber to an outlet region of the second vacuum pump, and wherein the first vacuum pump is arranged and configured for pumping gas from the outlet region of the second vacuum pump to an outlet of the first vacuum pump so as to reduce the pressure of the outlet region of the second vacuum pump;
detecting means for determining when the first vacuum pump causes the pressure within the first vacuum chamber to fall below a predetermined threshold; wherein the detecting means comprises means for monitoring the value of at least one parameter that varies with the variation of pressure within the first vacuum chamber, and means for determining when said parameter reaches a threshold value that is indicative of the pressure in the first vacuum chamber being at said predetermined threshold; and
signal means for indicating that said inlet orifice is at least partially blocked when said detecting means determines that the pressure within the first vacuum chamber has fallen below the predetermined threshold by determining that the parameter has reached said threshold value;
wherein one of said at least one parameters is the amount of power that the second vacuum pump is using or the amount of current that the second vacuum pump is drawing, and wherein the spectrometer is configured to signal that the inlet orifice is at least partially blocked when said power or current decreases to reach said threshold value; or
wherein the spectrometer further comprises a temperature sensor for monitoring the temperature of part of the second vacuum pump or a region in proximity to the second vacuum pump, wherein one of said at least one parameters is said temperature and the signal means is configured to signal that the inlet orifice is at least partially blocked when the temperature measured by the temperature sensor decreases to reach said threshold value.

The reason for a lack of sensitivity or a signal in a spectrometer is often not immediately apparent. The present invention provides a convenient and efficient technique for automatically detecting and indicating a full or partial blockage of the inlet orifice of the spectrometer. Such a blockage can therefore be cleaned out and the problem rectified with minimal disruption to the operation of the instrument and without further wastage of analyte samples.

The features of the present invention enable the blockage of the inlet orifice to be detected without directly measuring the pressure in the vacuum chambers. This is beneficial in that the difficulty and expensive of introducing a pressure gauge into the vacuum chamber are not encountered. The present invention may determine the presence of a blockage by measuring the current or power drawn by a vacuum pump. This is a particularly simple, non-invasive, but yet accurate method of determining the pressure in the vacuum chamber and hence of determining whether or not there is a blockage in the inlet orifice.

The term "inlet orifice" as used herein is intended to cover a simple orifice in the wall of a vacuum chamber as well as the orifice in an inlet capillary, a multibore capillary, or asymmetrical inlets etc.

The predetermined threshold pressure is a pressure that is indicative of a blockage in said inlet orifice.

Less preferably, the detecting means may comprise a pressure gauge for monitoring the pressure in the first vacuum chamber and may comprise means for determining when the measured pressure falls below the predetermined threshold pressure. A signal means may be configured to signal that the inlet orifice is at least partially blocked when the measured pressure falls below the predetermined threshold pressure. This technique therefore measures the pressure in the vacuum chamber directly in order to determine a presence of a blockage in the inlet orifice and hence is less preferred.

The second vacuum pump is arranged and configured for pumping gas from the second vacuum chamber to the outlet region of the second vacuum pump. The first vacuum pump is arranged and configured for pumping gas from the outlet region of the second vacuum pump to the outlet of the first vacuum pump so as to reduce the pressure of the outlet region of the second vacuum pump. This enables the second vacuum pump to pump the second vacuum chamber down to a very low pressure. For example, the first vacuum pump may be configured to pump the outlet region of the second vacuum pump down to a pressure of <100 mbar, <50 mbar, <20 mbar, <10 mbar or <5 mbar. The second vacuum pump is then able to pump the second vacuum chamber down to even lower pressures, e.g. that are optimised for the operation of ion mass analysers.

The first vacuum pump is preferably directly connected to the first vacuum chamber and preferably, in the above described embodiment, the first vacuum pump is also connected to the second vacuum pump.

The spectrometer preferably comprises a gas conduit extending between the first chamber and the first vacuum pump, wherein the outlet region of the second vacuum pump is either within or connected to said gas conduit at a point between said first chamber and said first vacuum pump. As such, when the first vacuum chamber drops in pressure due to a blockage, the demand on the second vacuum pump is reduced. The operational characteristics of the second vacuum pump can therefore be used to determine the pressure in the first vacuum chamber and hence to determine if there is a blockage in the inlet orifice.

The second vacuum pump is preferably a turbomolecular pump.

The first vacuum pump is preferably a roughing pump or a backing pump.

The second vacuum pump preferably maintains the second vacuum chamber at a lower pressure than the first vacuum chamber.

The first and second vacuum chambers are preferably interconnected by an orifice or other means for allowing ions to pass from the first vacuum chamber to the second vacuum chamber. The second vacuum chamber preferably houses at least one of: an ion guide, an ion trap, a mass analyser, and an ion mobility analyser.

The spectrometer may comprise a third vacuum pump arranged and configured for pumping gas from said first vacuum chamber to an outlet region of the third vacuum pump and/or for pumping gas from the outlet region of the second vacuum pump to an outlet of the third vacuum pump. The third vacuum pump may be a roughing pump or a backing pump.

As described above, the detecting means comprises means for monitoring the value of at least one parameter that varies with the variation of pressure within the first vacuum chamber. One of said at least one parameters is preferably the amount of power that the second vacuum pump is using or the amount of current that the second vacuum pump is drawing, and the spectrometer is preferably configured to signal that the inlet orifice is at least partially blocked when said power or current decreases to reach said threshold value.

Other parameters may be used, or combinations of different parameters may be used to determine the presence of a blockage in the inlet orifice.

For example, alternatively or additionally, the spectrometer may further comprise a temperature sensor for monitoring the temperature of part of the second vacuum pump or a region in proximity to the second vacuum pump, wherein one of said at least one parameters is said temperature and the signal means is configured to signal that the inlet orifice is at least partially blocked when the temperature measured by the temperature sensor decreases to reach said threshold value.

The spectrometer may comprise a first temperature sensor for monitoring the temperature of part of the second vacuum pump or a region in proximity to the second vacuum pump and a second temperature sensor for monitoring the temperature of the ambient air, wherein one of said at least one parameters is a temperature difference corresponding to the temperature of the second vacuum pump or region above the ambient air temperature, and the signal means is configured to signal that the inlet orifice is at least partially blocked when said temperature difference decreases to reach said threshold value.

Alternatively, or additionally, one of said at least one parameters may be the gas flow rate pumped out of the first chamber by the first vacuum pump, and the spectrometer may be configured to signal that the inlet orifice is at least partially blocked when said gas flow rate decreases to reach said threshold value.

Preferably, the detecting means is configured to determine when the first vacuum pump causes the pressure within the first vacuum chamber to fall below a relatively high threshold pressure and also below a relatively low threshold pressure. The spectrometer may be configured to signal a relatively low degree of blockage of the inlet orifice when the pressure falls below the high threshold pressure and a relatively high degree of blockage when the pressure falls below the low threshold pressure. Such a spectrometer is therefore able to indicate the level of blockage of the inlet orifice. The signalling means may use this to indicate the urgency with which the inlet orifice should be cleaned. Although two threshold levels have been described, more than two thresholds may be used to indicate more than two levels of blockage of the inlet orifice.

The ion source is preferably coupled to a liquid chromatography column for ionising analyte eluting from the column. However, other types of ion source are also contemplated, as other ion sources also lead to blockage of the inlet orifice.

The ion source is preferably an atmospheric pressure ion source.

The inlet orifice is preferably an atmospheric pressure inlet.

The first vacuum chamber is preferably the inlet chamber of the spectrometer.

It is also contemplated that an ion source and/or inlet orifice that operates at a lower pressure may be used in the present invention. The technique of the present invention is useful provided that the pressures on either side of the inlet orifice are such that there is a gas flow through the inlet orifice and into the vacuum chamber, since it is a restriction in this gas flow that is used to determine the presence of a blockage in the inlet orifice.

The inlet orifice is preferably arranged in a wall of the first vacuum chamber and/or the inlet orifice is directly adjacent to the ion source. Preferably, no other vacuum chambers or pumped regions are arranged between said first vacuum chamber and said inlet orifice.

The second vacuum chamber is preferably arranged downstream of the first vacuum chamber, and the spectrometer is preferably configured such that the second vacuum chamber is pumped to a lower pressure than the first vacuum chamber.

The spectrometer comprises a mass analyser or ion mobility separator, which may be arranged in said second vacuum chamber.

From a second aspect the present invention provides a mass spectrometer or ion mobility spectrometer comprising:
an ion source;
a first vacuum chamber;
a first vacuum pump for maintaining the pressure within the vacuum chamber lower than the pressure outside of the chamber;
an inlet orifice arranged between the ion source and the vacuum chamber for allowing ions to pass from the ion source into the vacuum chamber;

detecting means for determining when the vacuum pump causes the pressure within the vacuum chamber to fall below a predetermined threshold; wherein the detecting means comprises means for monitoring the value of at least one parameter that varies with the variation of pressure within the first vacuum chamber, and means for determining when said parameter reaches a threshold value that is indicative of the pressure in the first vacuum chamber being at said predetermined threshold, wherein one of said at least one parameters is the gas flow rate pumped out of the first vacuum chamber by the first vacuum pump; and signal means for indicating that said inlet orifice is at least partially blocked when said detecting means determines that the pressure within the vacuum chamber has fallen below the predetermined threshold by determining that said gas flow rate has decreased to reach said threshold value.

The spectrometer of the second aspect may have any one, or any combination of any two or more, of the optional or preferred features described in relation to the first aspect of the present invention.

According to the first aspect, the present invention also provides a method of detecting a blockage in a mass spectrometer or ion mobility spectrometer comprising:

providing a mass spectrometer or ion mobility spectrometer having an ion source, a first vacuum chamber, a first vacuum pump, an inlet orifice arranged between the ion source and the vacuum chamber for allowing ions to pass from the ion source into the vacuum chamber, a second vacuum chamber and a second vacuum pump;

operating the first vacuum pump so as to reduce the pressure in the first vacuum chamber relative to the ambient pressure;

operating the second vacuum pump to pump gas from the second vacuum chamber to an outlet region of the second vacuum pump, wherein the first vacuum pump pumps gas from the outlet region of the second vacuum pump to an outlet of the first vacuum pump so as to reduce the pressure of the outlet region of the second vacuum pump;

determining when the first vacuum pump causes the pressure within the first vacuum chamber to fall below a predetermined threshold, comprising monitoring the value of at least one parameter that varies with the variation of pressure within the first vacuum chamber, and determining when said parameter reaches a threshold value that is indicative of the pressure in the first vacuum chamber being at said predetermined threshold; and signalling that said inlet orifice is at least partially blocked when it is determined that the pressure within the first vacuum chamber has fallen below the predetermined threshold by determining that the parameter has reached said threshold value;

wherein one of said at least one parameters is the amount of power that the second vacuum pump is using or the amount of current that the second vacuum pump is drawing, and wherein the spectrometer signals that the inlet orifice is at least partially blocked when said power or current decreases to reach said threshold value; or wherein the spectrometer further comprises a temperature sensor that monitors the temperature of part of the second vacuum pump or a region in proximity to the second vacuum pump, wherein one of said at least one parameters is said temperature and the spectrometer signals that the inlet orifice is at least partially blocked when the temperature measured by the temperature sensor decreases to reach said threshold value.

The method less preferably comprises: monitoring the pressure within the first vacuum chamber using a pressure gauge; determining when the measured pressure falls below the predetermined threshold pressure; and signalling that the inlet orifice is at least partially blocked when the measured pressure falls below the predetermined threshold pressure.

The first vacuum pump may pump the outlet region of the second vacuum pump down to a pressure of <100 mbar, <50 mbar, <20 mbar, <10 mbar or <5 mbar. The first vacuum pump is preferably directly connected to the first vacuum chamber and also to the outlet of the second vacuum pump.

The method preferably also comprises providing a gas conduit extending between the first chamber and the first vacuum pump, wherein the outlet region of the second vacuum pump is either within or connected to said gas conduit at a point between said first chamber and said first vacuum pump.

The second vacuum pump is preferably a turbomolecular pump.

The first vacuum pump is preferably a roughing pump or a backing pump.

The second vacuum pump preferably maintains the second vacuum chamber at a lower pressure than the first vacuum chamber.

The first and second vacuum chambers are preferably interconnected by an orifice and ions are passed from the first vacuum chamber to the second vacuum chamber.

The second vacuum chamber preferably houses at least one of: an ion guide, an ion trap, a mass analyser, and an ion mobility analyser for manipulating the ions.

The spectrometer may comprise a third vacuum pump arranged and configured for pumping gas from said first vacuum chamber to an outlet region of the third vacuum pump and/or for pumping gas from the outlet region of the second vacuum pump to an outlet of the third vacuum pump. The third vacuum pump may be a roughing pump or a backing pump.

One of said at least one parameters is preferably the amount of power that the second vacuum pump is using or the amount of current that the second vacuum pump is drawing, and the spectrometer preferably signals that the inlet orifice is at least partially blocked when said power or current decreases to reach said threshold value.

The method may comprise: monitoring the temperature of part of the second vacuum pump or a region in proximity to the second vacuum pump, wherein said parameter is said temperature; and signalling that the inlet orifice is at least partially blocked when the temperature measured by the temperature sensor decreases to reach said threshold value.

The method may comprise: monitoring the temperature of part of the second vacuum pump or a region in proximity to the second vacuum pump and monitoring the temperature of the ambient air, wherein the parameter is a temperature difference corresponding to the temperature of the second vacuum pump or region above the ambient air temperature; and signalling that the inlet orifice is at least partially blocked when said temperature difference decreases to reach said threshold value.

The parameter may be the gas flow rate pumped out of the first vacuum chamber by the first vacuum pump, and the method may signal that the inlet orifice is at least partially blocked when said gas flow rate decreases to reach said threshold value.

The method may determine when the first vacuum pump causes the pressure within the first vacuum chamber to fall below a relatively high threshold pressure and also below a relatively low threshold pressure, and to signal a relatively low degree of blockage of the inlet when the pressure falls below the high threshold pressure and a relatively high degree of blockage when the pressure falls below the low threshold pressure.

The method may comprise ionising a sample eluting from a liquid chromatography column.

The method may comprise operating the ion source substantially at atmospheric pressure.

The method may comprise operating the inlet orifice substantially at atmospheric pressure.

The method may use any spectrometer as described herein.

The method may further comprise mass analysing ions or performing ion mobility separation and analysis on ions within the spectrometer, preferably within said second vacuum chamber.

The spectrometer preferably comprises a miniature mass spectrometer or a miniature ion mobility spectrometer. This present invention is particularly useful in, although not limited to, miniature spectrometers as such spectrometer inlet orifices are relatively small and the likelihood of these becoming blocked is relatively high. Blockages to these inlet orifices can often be invisible to the naked eye when in use and so an automated method of alerting the user to such blocking is highly advantageous.

The inlet orifice of the present invention may have a diameter of <1.2 mm; <1.0 mm; <0.8 mm; <0.6 mm; <0.5 mm; <0.4 mm; <0.3 mm; <0.25 mm; <0.2 mm; <0.15 mm; <0.10 mm; or <0.05 mm.

The inlet orifice of the present invention may have an area of <1.15 $mm^2$; <1.0 $mm^2$; <0.9 $mm^2$; <0.8 $mm^2$; <0.7 $mm^2$; <0.6 $mm^2$; <0.5 $mm^2$; <0.4 $mm^2$; <0.3 $mm^2$; <0.2 $mm^2$; <0.10 $mm^2$; <0.08 $mm^2$; <0.07 $mm^2$; <0.06 $mm^2$; <0.05 $mm^2$; <0.04 $mm^2$; <0.03 $mm^2$; or <0.02 $mm^2$.

The inlet orifice dimensions above preferably refer to an inlet orifice in the form of a circular or other shaped aperture.

According to the second aspect, the present invention also provides a method of detecting a blockage in a mass spectrometer or ion mobility spectrometer comprising:

providing a mass spectrometer or ion mobility spectrometer having an ion source, a first vacuum chamber, a first vacuum pump, and an inlet orifice arranged between the ion source and the vacuum chamber for allowing ions to pass from the ion source into the vacuum chamber;

operating the vacuum pump so as to reduce the pressure in the vacuum chamber relative to the ambient pressure;

determining when the vacuum pump causes the pressure within the vacuum chamber to fall below a predetermined threshold, comprising monitoring the value of at least one parameter that varies with the variation of pressure within the vacuum chamber, and determining when said parameter reaches a threshold value that is indicative of the pressure in the vacuum chamber being at said predetermined threshold, wherein one of said at least one parameters is the gas flow rate pumped out of the vacuum chamber by the vacuum pump; and signalling that said inlet orifice is at least partially blocked when it is determined that the pressure within the vacuum chamber has fallen below the predetermined threshold by determining that said gas flow rate has decreased to reach said threshold value.

The method of the second aspect may have any one, or any combination of any two or more, of the optional or preferred features described in relation to the first aspect of the present invention.

The spectrometer of the present invention may comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; and (xxvi) a Solvent Assisted Inlet Ionisation ("SAII") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic or orbitrap mass analyser; (x) a Fourier Transform electrostatic or orbitrap mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The spectrometer may further comprise either:

(i) a C-trap and an Orbitrap® mass analyser comprising an outer barrel-like electrode and a coaxial inner spindle-like electrode, wherein in a first mode of operation ions are transmitted to the C-trap and are then injected into the Orbitrap® mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the Orbitrap® mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

The spectrometer may further comprise a device arranged and adapted to supply an AC or RF voltage to the electrodes. The AC or RF voltage preferably has an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage preferably has a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

As described above, the blockage in the inlet orifice is preferably detected by determining the amount of power that the second vacuum pump is using, the amount of current that the second vacuum pump is drawing, the temperature of part of the second vacuum pump, the temperature of a region in proximity to the second vacuum pump, or the gas flow rate pumped out of the first vacuum chamber by the first vacuum pump. However, it is contemplated that the blockage may be detected by other means, for example, by directly measuring the pressure in the first chamber with a pressure gauge.

Accordingly, the present invention provides a mass spectrometer or ion mobility spectrometer comprising:

an ion source;

a first vacuum chamber;

a first vacuum pump for maintaining the pressure within the vacuum chamber lower than the pressure outside of the chamber;

an inlet orifice arranged between the ion source and the vacuum chamber for allowing ions to pass from the ion source into the vacuum chamber;

detecting means for determining when the vacuum pump causes the pressure within the vacuum chamber to fall below a predetermined threshold; and signal means for indicating that said inlet orifice is at least partially blocked when said detecting means determines that the pressure within the vacuum chamber has fallen below the predetermined threshold.

The spectrometer may comprise any one, or any combination of any two or more, of the optional or preferred features described in relation to the first or second aspects of the present invention.

For example, the detecting means may comprise a pressure gauge for monitoring the pressure in the first vacuum chamber and comprises means for determining when the measured pressure falls below the predetermined threshold pressure, and wherein the signal means is configured to signal that the inlet orifice is at least partially blocked when the measured pressure falls below the predetermined threshold pressure.

Similarly, the present invention also provides a method of detecting a blockage in a mass spectrometer or ion mobility spectrometer comprising:

providing a mass spectrometer or ion mobility spectrometer having an ion source, a first vacuum chamber, a first vacuum pump, and an inlet orifice arranged between the ion source and the vacuum chamber for allowing ions to pass from the ion source into the vacuum chamber;

operating the vacuum pump so as to reduce the pressure in the vacuum chamber relative to the ambient pressure;

determining when the vacuum pump causes the pressure within the vacuum chamber to fall below a predetermined threshold; and signalling that said inlet orifice is at least partially blocked when it is determined that the pressure within the vacuum chamber has fallen below the predetermined threshold.

BRIEF DESCRIPTION OF THE DRAWINGS

Various embodiments of the present invention will now be described, by way of example only, and with reference to the accompanying drawings in which.

DETAILED DESCRIPTION OF PREFERRED EMBODIMENTS

Figure 1:
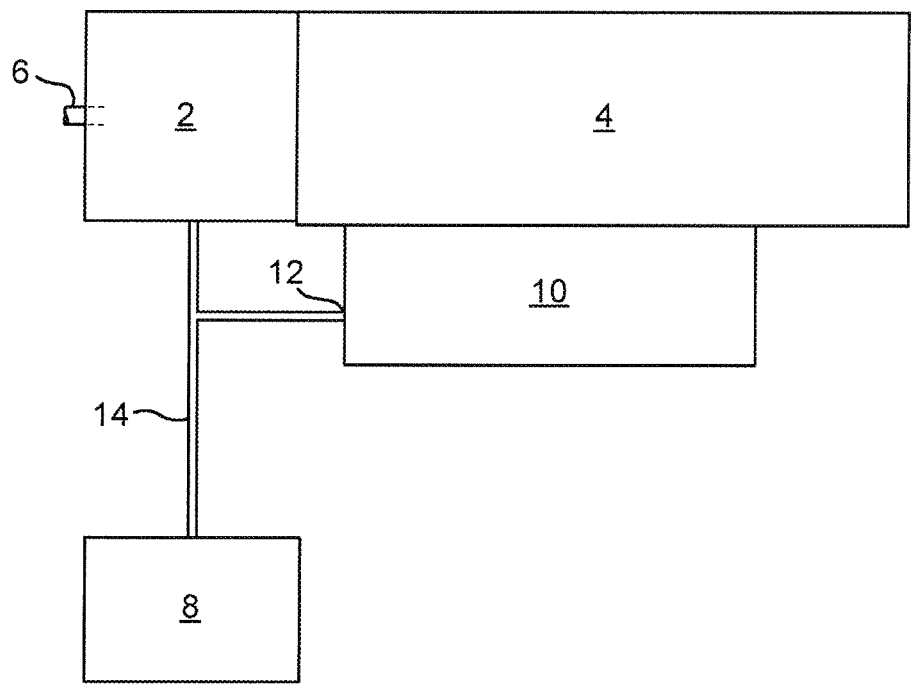
FIG. 1 shows a schematic of a spectrometer that uses a single roughing pump.

FIG. 1 illustrates part of a spectrometer according to a preferred embodiment of the present invention. The spectrometer comprises a first chamber 2 and a second chamber 4. An inlet orifice 6 is provided in the first chamber so as to allow ions to enter the first chamber from an ion source (not shown). A mass analyser or ion mobility analyser (not shown) is arranged in the second chamber. An orifice (not shown) is arranged in the wall between the first and second chambers such that the ions can pass from the first chamber into the second chamber and then be analysed in the mass analyser or ion mobility analyser. A first vacuum pump 8, known in the art as a roughing pump or backing pump, is connected to the first chamber for evacuating the first chamber. This pump reduces the pressure in the first chamber to a pressure below atmospheric pressure. The roughing pump may be, for example, a rotary pump or a diaphragm pump. A second vacuum pump 10, known in the art as a turbomolecular pump, is connected to the second chamber for evacuating the second chamber to a pressure below atmospheric pressure.

It is typically desired to reduce the pressure in the second chamber to a very low pressure in order for the analyser housed therein to operate optimally. This is achieved using a turbomolecular pump. However, turbomolecular pumps are not able to pump gas from a chamber out to a region that is at atmospheric pressure. Rather, turbomolecular pumps are only able to pump gas out into a region that is at a pressure of a few milli-bars. Accordingly, the roughing pump is connected to the outlet 12 of the turbomolecular pump so that the roughing pump can pump the outlet of the turbo-down to a pressure of a few milli-bars. This process is known in the art as the roughing pump (also known as a backing pump) backing the turbomolecular pump.

It will be appreciated that it is easier to evacuate the second chamber, which houses the analyser, down to the desired pressure since the second chamber is connected to the first chamber, which has already been reduced in pressure by the roughing pump.

The spectrometer preferably comprises a liquid chromatography column and an ionisation source (not shown) that operates at close to atmospheric pressure so as to ionise the sample that elutes from the liquid chromatography column. The ionisation source is arranged upstream of the inlet orifice to the first chamber. Ions pass from the high pressure ion source into the lower pressure first chamber of the spectrometer via the inlet orifice. The ions are therefore preferably sampled by an atmospheric pressure inlet orifice. The ions then pass to the lower pressure, turbomolecular pumped second chamber in order to be analysed by the analyser.

Over time, the sample, matrix and other contaminants within the liquid chromatography eluent cause the inlet orifice to become partially or fully blocked. This leads to a decreased sensitivity of the spectrometer, although the operator may not be aware that the decreased sensitivity has been caused by the blockage. The preferred embodiments of the present invention are able to detect and indicate the presence of such blockages to the operator, as will be described below.

According to a preferred embodiment, the pressure in the first chamber is monitored indirectly. If the inlet orifice becomes partially or fully blocked, the pressure in the first chamber decreases to a lower value than would be otherwise expected, because the roughing pump continues to pump gas out of the first chamber at substantially the same rate, but less gas is drawn into the first chamber as the size of the inlet orifice 6 has been restricted by the blockage. It can therefore be determined when the inlet orifice has become blocked by selecting a predetermined threshold for the pressure in the first chamber that is indicative of a blocked inlet orifice, and determining when the pressure inside the first chamber has dropped to this threshold pressure. When the pressure falls to this threshold value the spectrometer signals an alert to the operator to indicate that the operator should take appropriate action, such as clean the inlet orifice.

Figure 2:
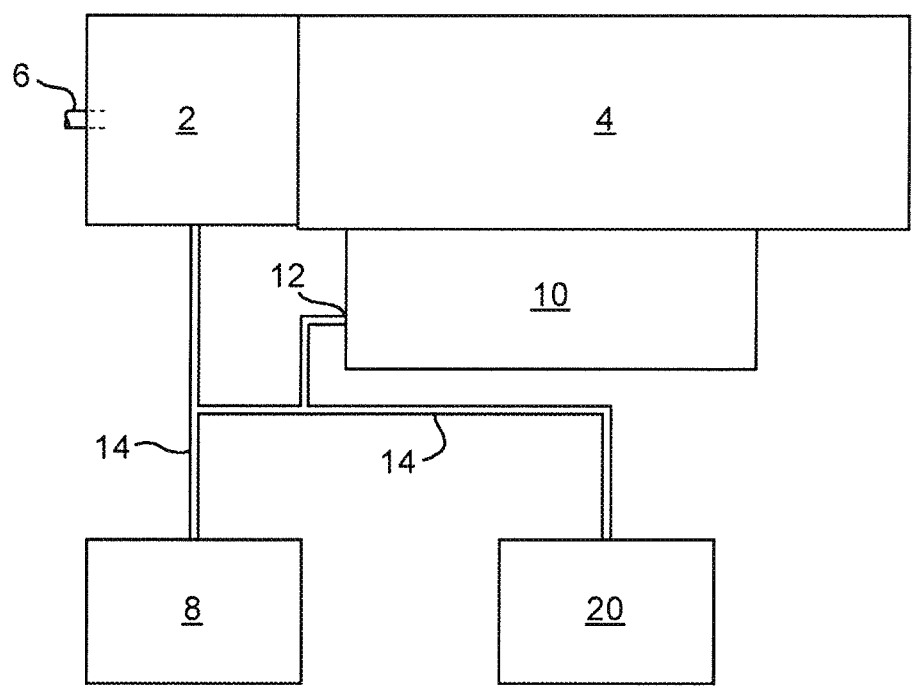
FIG. 2 shows a schematic of a spectrometer that uses two roughing pumps.

FIG. 2 shows another embodiment that is the same as that depicted in FIG. 1, except that the spectrometer includes a second roughing pump 20. Both the first and second roughing pumps 8,20 are connected to the first chamber 2 so as to evacuate the first chamber. Both of the roughing pumps are also connected to the outlet 12 of the turbomolecular pump. This allows both roughing pumps (also known as backing pumps) to back the turbomolecular pump 10 such that the outlet of the turbomolecular pump is at the desired pressure for the turbomolecular pump to operate efficiently and so as to enable the turbomolecular pump to evacuate the second chamber 4 to the desired pressure. Each of the roughing pumps may be a rotary pump or a diaphragm pump.

Although the pressure in the first chamber may be measured directly, it is contemplated that the pressure be monitored indirectly so as to determine the presence of a blockage in the inlet orifice. These alternative embodiments include the monitoring of other parameters that are indicative of a decrease in pressure in the first chamber due to the inlet orifice being restricted, rather than monitoring the pressure of the first chamber directly.

For example, a parameter that is indicative of the pressure in the first chamber 2 and which may be monitored in order to determine the presence of a blockage in the inlet orifice 6 is the electrical power or current drawn by the turbomolecular pump 10. Referring to FIGS. 1 and 2 to illustrate this principle, if the inlet orifice in the first chamber becomes partially or fully blocked then the pressure in the first chamber will drop because the roughing pump(s) 8,20 connected to the first chamber continue to evacuate the first chamber but the flow of gas into the first chamber through the inlet orifice is restricted by the blockage. As the first chamber has dropped in pressure, the pressure in the outlet path(s) 14 between the first chamber and the roughing pump(s) decreases. The output region of the turbomolecular pump 12 is connected to the outlet path(s) that extend between the first chamber and the roughing pump(s) and as such the output region of the turbomolecular pump also reduces in pressure. Therefore, when the pressure in the first chamber drops the turbomolecular pump is not required to work as hard in order to evacuate the second chamber. The electrical power or current required by the turbomolecular pump to maintain the desired pressure in the second chamber is therefore reduced. Hence, the pressure in the first chamber can be indirectly determined by monitoring the amount of electrical power or current being drawn by the turbomolecular pump. When the power or current drawn by the turbomolecular pump drops to a predetermined threshold level it is considered that the pressure in the first chamber is at a pressure which indicates that the inlet orifice has become blocked. The spectrometer then signals to an operator that the inlet orifice requires cleaning.

Another parameter that is indicative of the pressure in the first chamber and which may be monitored in order to determine the presence of a blockage in the inlet orifice is the temperature of the turbomolecular pump. As in the above example, if the inlet orifice in the first chamber becomes partially or fully blocked then the turbomolecular pump does not have to work as hard in order to maintain the second chamber at its desired low pressure. As the turbomolecular pump begins to work less hard, the temperature of the turbomolecular pump reduces. Hence, the pressure in the first chamber can be indirectly determined by monitoring the temperature of the turbomolecular pump. When the temperature of the turbomolecular pump drops to a predetermined threshold level it is considered that the pressure in the first chamber is at a pressure which indicates that the inlet orifice is blocked. The spectrometer then signals to an operator that the inlet orifice requires cleaning. The temperature being monitored and the threshold temperature that triggers the signal to clean the inlet orifice may be an absolute temperature or it may be the temperature difference relative to another component or region. For example, the temperature difference of the turbomolecular pump relative to ambient air may be monitored and when the difference reduces to a threshold level the inlet orifice may be determined to be blocked.

Another parameter that is indicative of the pressure in the first chamber and which may be monitored in order to determine the presence of a blockage in the inlet orifice is the rotational speed of the turbomolecular pump. As in the above example, if the inlet orifice in the first chamber becomes partially or fully blocked then the output region of the turbomolecular pump also reduces in pressure and so it is easier for the turbomolecular pump to evacuate the second chamber. Therefore, for a given rate of power consumption by the turbomolecular pump, the rotational speed of the turbomolecular pump will increase when the pressure in the first chamber decreases. Hence, the pressure in the first chamber can be indirectly determined by monitoring the rotational speed of the turbomolecular pump. When the rotational speed of the turbomolecular pump increases to a predetermined threshold level it is considered that the pressure in the first chamber is at a pressure which indicates that the inlet orifice is blocked. The spectrometer then signals to an operator that the inlet orifice requires cleaning.

The above embodiments are able to determine the drop in pressure in the first chamber indirectly, i.e. without measuring the pressure per se. These embodiments therefore do not require a backing pressure gauge and hence reduce the cost of the spectrometer. This is achieved in the above embodiments by using at least one roughing pump to pump both the first chamber and the outlet region of the turbo-molecular pump.

This present invention is particularly useful in, although not limited to, miniature spectrometers as such spectrometer inlet orifices are relatively small and the likelihood of these becoming blocked is relatively high. Blockages to these inlet orifices can often be invisible to the naked eye when in use and so an automated method of alerting the user to such blocking is highly advantageous.

Although the present invention has been described with reference to preferred embodiments, it will be understood by those skilled in the art that various changes in form and detail may be made without departing from the scope of the invention as set forth in the accompanying claims.

The invention claimed is:

1. A mass spectrometer or ion mobility spectrometer comprising:

an ion source;
a first vacuum chamber;
a first vacuum pump for maintaining the pressure within the vacuum chamber lower than the pressure outside of the chamber;
an inlet orifice arranged between the ion source and the vacuum chamber for allowing ions to pass from the ion source into the vacuum chamber;
a second vacuum pump and a second vacuum chamber, wherein the second vacuum pump is arranged and configured for pumping gas from the second vacuum chamber to an outlet region of the second vacuum pump, and wherein the first vacuum pump is arranged and configured for pumping gas from the outlet region of the second vacuum pump to an outlet of the first vacuum pump so as to reduce the pressure of the outlet region of the second vacuum pump;
detecting means for determining when the first vacuum pump causes the pressure within the first vacuum chamber to fall below a predetermined threshold; wherein the detecting means comprises means for monitoring the value of at least one parameter that varies with the variation of pressure within the first vacuum chamber, and means for determining when said parameter reaches a threshold value that is indicative of the pressure in the first vacuum chamber being at said predetermined threshold; and
signal means for indicating that said inlet orifice is at least partially blocked when said detecting means determines that the pressure within the first vacuum chamber has fallen below the predetermined threshold by determining that the parameter has reached said threshold value;
wherein one of said at least one parameters is the amount of power that the second vacuum pump is using or the amount of current that the second vacuum pump is drawing, and wherein the spectrometer is configured to signal that the inlet orifice is at least partially blocked when said power or current decreases to reach said threshold value; or
wherein the spectrometer further comprises a temperature sensor for monitoring the temperature of part of the second vacuum pump or a region in proximity to the second vacuum pump, wherein one of said at least one parameters is said temperature and the signal means is configured to signal that the inlet orifice is at least partially blocked when the temperature measured by the temperature sensor decreases to reach said threshold value.

2. The spectrometer of claim 1, wherein the detecting means comprises a pressure gauge for monitoring the pressure in the first vacuum chamber and comprises means for determining when the measured pressure falls below the predetermined threshold pressure, and wherein the signal means is configured to signal that the inlet orifice is at least partially blocked when the measured pressure falls below the predetermined threshold pressure.

3. The spectrometer of claim 1, comprising a gas conduit extending between the first vacuum chamber and the first vacuum pump, wherein the outlet region of the second vacuum pump is either within or connected to said gas conduit at a point between said first vacuum chamber and said first vacuum pump.

4. The spectrometer of claim 1, wherein the second vacuum pump is a turbomolecular pump.

5. The spectrometer of claim 1, wherein said first and second vacuum chambers are interconnected by an orifice for allowing ions to pass from the first vacuum chamber to the second vacuum chamber, and wherein the second vacuum chamber houses at least one of: an ion guide, an ion trap, an ion mass analyser, and an ion mobility analyser.

6. The spectrometer of claim 1, further comprising a first temperature sensor for monitoring the temperature of part of the second vacuum pump or a region in proximity to the second vacuum pump and a second temperature sensor for monitoring the temperature of the ambient air, wherein one of said at least one parameters is a temperature difference corresponding to the temperature of the second vacuum pump or region above the ambient air temperature, and the signal means is configured to signal that the inlet orifice is at least partially blocked when said temperature difference decreases to reach said threshold value.

7. The spectrometer of claim 1, wherein one of said at least one parameters is the gas flow rate pumped out of the first vacuum chamber by the first vacuum pump, and wherein the spectrometer is configured to signal that the inlet orifice is at least partially blocked when said gas flow rate decreases to reach said threshold value.

8. The spectrometer of claim 1, wherein the detecting means is configured to determine when the first vacuum pump causes the pressure within the first vacuum chamber to fall below a relatively high threshold pressure and also below a relatively low threshold pressure, wherein the spectrometer is configured to signal a relatively low degree of blockage of the inlet orifice when the pressure falls below the high threshold pressure and a relatively high degree of blockage when the pressure falls below the low threshold pressure.

9. The spectrometer of claim 1, wherein the ion source is coupled to a liquid chromatography column for ionising analyte eluting from the column.

10. The spectrometer of claim 1, wherein the inlet orifice is arranged in a wall of the first vacuum chamber and/or the inlet orifice is directly adjacent to the ion source.

11. A mass spectrometer as claimed in claim 1, wherein said mass spectrometer comprises a miniature mass spectrometer.

12. A mass spectrometer or ion mobility spectrometer comprising:
an ion source;
a first vacuum chamber;
a first vacuum pump for maintaining the pressure within the vacuum chamber lower than the pressure outside of the chamber;
an inlet orifice arranged between the ion source and the vacuum chamber for allowing ions to pass from the ion source into the vacuum chamber;
detecting means for determining when the vacuum pump causes the pressure within the vacuum chamber to fall below a predetermined threshold; wherein the detecting means comprises means for monitoring the value of at least a parameter that varies with the variation of pressure within the first vacuum chamber, and means for determining when said parameter reaches a threshold value that is indicative of the pressure in the first vacuum chamber being at said predetermined threshold, wherein said parameter is the gas flow rate pumped out of the first vacuum chamber by the first vacuum pump; and
signal means for indicating that said inlet orifice is at least partially blocked when said detecting means determines that the pressure within the vacuum chamber has fallen below the predetermined threshold by determining that said gas flow rate has decreased to reach said threshold value.

13. The spectrometer of claim 12, wherein the detecting means is configured to determine when the first vacuum pump causes the pressure within the first vacuum chamber to fall below a relatively high threshold pressure and also below a relatively low threshold pressure, wherein the spectrometer is configured to signal a relatively low degree of blockage of the inlet orifice when the pressure falls below the high threshold pressure and a relatively high degree of blockage when the pressure falls below the low threshold pressure.

14. The spectrometer of claim 12, wherein the ion source is coupled to a liquid chromatography column for ionising analyte eluting from the column.

15. The spectrometer of claim 12, wherein the inlet orifice is arranged in a wall of the first vacuum chamber and/or the inlet orifice is directly adjacent to the ion source.

16. A method of detecting a blockage in a mass spectrometer or ion mobility spectrometer comprising:
providing a mass spectrometer or ion mobility spectrometer having an ion source, a first vacuum chamber, a first vacuum pump, an inlet orifice arranged between the ion source and the vacuum chamber for allowing ions to pass from the ion source into the vacuum chamber, a second vacuum chamber and a second vacuum pump;
operating the first vacuum pump so as to reduce the pressure in the first vacuum chamber relative to the ambient pressure;
operating the second vacuum pump to pump gas from the second vacuum chamber to an outlet region of the second vacuum pump, wherein the first vacuum pump pumps gas from the outlet region of the second vacuum pump to an outlet of the first vacuum pump so as to reduce the pressure of the outlet region of the second vacuum pump; determining when the first vacuum pump causes the pressure within the first vacuum chamber to fall below a predetermined threshold, comprising monitoring the value of at least one parameter that varies with the variation of pressure within the first vacuum chamber, and determining when said parameter reaches a threshold value that is indicative of the pressure in the first vacuum chamber being at said predetermined threshold; and
signalling that said inlet orifice is at least partially blocked when it is determined that the pressure within the first vacuum chamber has fallen below the predetermined threshold by determining that the parameter has reached said threshold value;
wherein one of said at least one parameters is the amount of power that the second vacuum pump is using or the amount of current that the second vacuum pump is drawing, and wherein the spectrometer signals that the inlet orifice is at least partially blocked when said power or current decreases to reach said threshold value; or
wherein the spectrometer further comprises a temperature sensor that monitors the temperature of part of the second vacuum pump or a region in proximity to the second vacuum pump, wherein one of said at least one parameters is said temperature and the spectrometer signals that the inlet orifice is at least partially blocked when the temperature measured by the temperature sensor decreases to reach said threshold value.

\* \* \* \* \*